United States Patent
Neufang et al.

(10) Patent No.: US 9,789,099 B2
(45) Date of Patent: Oct. 17, 2017

(54) COSMETIC OR DERMATOLOGICAL PREPARATION FOR PROPHYLAXIS AND/OR TREATMENT OF ATOPIC DERMATITIS

(71) Applicant: Beiersdorf AG, Hamburg (DE)

(72) Inventors: Gitta Neufang, Hamburg (DE); Torsten Schlaeger, Hamburg (DE); Nadine Voigt, Hamburg (DE); Anne-Christin Worthmann, Hasloh (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 14/433,455

(22) PCT Filed: Sep. 10, 2013

(86) PCT No.: PCT/EP2013/068674
§ 371 (c)(1),
(2) Date: Apr. 3, 2015

(87) PCT Pub. No.: WO2014/060150
PCT Pub. Date: Apr. 24, 2014

(65) Prior Publication Data
US 2015/0258079 A1  Sep. 17, 2015

(30) Foreign Application Priority Data
Oct. 15, 2012 (DE) .......... 10 2012 218 733

(51) Int. Cl.
| | | |
|---|---|---|
| A61K 31/045 | (2006.01) |
| A61K 31/075 | (2006.01) |
| A61K 31/4402 | (2006.01) |
| A61K 9/00 | (2006.01) |
| A61K 47/10 | (2017.01) |
| A61K 45/06 | (2006.01) |
| A61K 31/085 | (2006.01) |
| A61K 31/11 | (2006.01) |
| A61K 31/12 | (2006.01) |
| A61K 31/166 | (2006.01) |
| A61K 31/215 | (2006.01) |
| A61K 31/22 | (2006.01) |
| A61K 9/06 | (2006.01) |

(52) U.S. Cl.
CPC ........ *A61K 31/4402* (2013.01); *A61K 9/0014* (2013.01); *A61K 31/045* (2013.01); *A61K 31/075* (2013.01); *A61K 31/085* (2013.01); *A61K 31/11* (2013.01); *A61K 31/12* (2013.01); *A61K 31/166* (2013.01); *A61K 31/215* (2013.01); *A61K 31/22* (2013.01); *A61K 45/06* (2013.01); *A61K 47/10* (2013.01); *A61K 9/06* (2013.01)

(58) Field of Classification Search
CPC .... A61K 31/085; A61K 31/11; A61K 31/166; A61K 31/215; A61K 31/22; A61K 31/075; A61K 31/4402; A61K 45/06; A61K 47/10; A61K 9/0014; A61K 9/06

USPC ......... 514/22, 171, 357, 369, 456, 629, 685, 514/715, 739

See application file for complete search history.

(56) References Cited

U.S. PATENT DOCUMENTS

| | | | |
|---|---|---|---|
| 6,649,178 B2 * | 11/2003 | Mohammadi | A61K 8/19 424/400 |
| 8,529,915 B2 * | 9/2013 | Wei | A61K 31/045 424/400 |
| 2006/0263452 A1 | 11/2006 | Dowell | |
| 2008/0253973 A1 | 10/2008 | Tamarkin et al. | |
| 2009/0297468 A1 | 12/2009 | Vielhaber et al. | |
| 2010/0305214 A1 | 12/2010 | D'Alessio | |
| 2012/0039823 A1 | 2/2012 | Kolbe et al. | |
| 2012/0053152 A1 * | 3/2012 | Wei | A61K 31/045 514/120 |
| 2012/0121737 A1 * | 5/2012 | Vielhaber | A23C 9/1307 424/737 |
| 2012/0237453 A1 | 9/2012 | Tamarkin et al. | |

FOREIGN PATENT DOCUMENTS

| | | | | |
|---|---|---|---|---|
| DE | 19824681 A1 | 12/1999 | | |
| DE | 202007015195 U1 | 8/2008 | | |
| DE | WO 2012143576 A2 * | 10/2012 | .......... | A61K 9/0014 |
| KR | 1049788 B1 | 7/2011 | | |
| WO | 9801134 A1 | 1/1998 | | |
| WO | 03092697 A1 | 11/2003 | | |
| WO | 2006134013 A1 | 12/2006 | | |
| WO | 2009040420 A2 | 4/2009 | | |
| WO | 2009127282 A1 | 10/2009 | | |

OTHER PUBLICATIONS

Bavencoffe et al., "The Transient Receptor Potential Channel TRPM8 Is Inhibited via the a2A Adrenoreceptor Signaling Pathway", 2010, Journal of Biological Chemistry, 285(13), pp. 9410-9419.*

Behrendt et al., "Characterization of the mouse cold-menthol receptor TRPM8 and vanilloid receptor type-1 VR1 using a fluorometric imaging plate reader (FLIPR) assay", 2004, British Journal of Pharmacology, vol. 141 (4), pp. 737-745.*

Sonali S. Bharate et al: "Modulation of Thermoreceptor TRPM8 by Cooling Compounds", ACS Chemical Neuroscience, vol. 3, No. 4, Apr. 18, 2012, pp. 248-267.

* cited by examiner

Primary Examiner — My-Chau T Tran
(74) Attorney, Agent, or Firm — Abel Law Group, LLP

(57) ABSTRACT

Agonists for the TRPM-8 receptor, more particularly one or more substances selected from the group of, for example, linalool, geraniol, hydroxycitronellal, WS-3 (N-ethyl-p-menthane-3-carboxamide), WS-23 (2-isopropyl-N,2,3-trimethylbutyramide), Frescolat MAG (1,4-dioxaspiro[4.5]decane-2-methanol), Frescolat ML (menthyl lactate), Coolact P (5-methyl-2-prop-1-en-2-ylcyclohexan-1-ol) and Cooling Agent 10 (menthoxypropanediol), for use as medicaments to counter atopic dermatitis.

20 Claims, No Drawings

COSMETIC OR DERMATOLOGICAL PREPARATION FOR PROPHYLAXIS AND/OR TREATMENT OF ATOPIC DERMATITIS

BACKGROUND OF THE INVENTION

Field of the Invention

The present invention relates to a preparation for external application which is used as a therapeutic agent for the prophylactic treatment or for the improvement of atopic dermatitis.

Discussion of Background Information

Atopic dermatitis is known as a type-I allergic reaction reacting to IgE. Various external preparations for the therapeutic treatment of atopic skin disease have been developed to date which comprises a compound with an activity for the inhibition of PCA reactions which reacts on IgE as an active ingredient.

In practical application, however, none is known which is adequately effective, while steroids, such as for example adrenocorticoidal hormones, furthermore constitutes the bulk of external preparations for therapeutic treatment of atopic skin diseases.

Although the steroids which are currently used for atopic dermatitis, which are used for skin disorders and other skin disorders, have excellent therapeutic efficacy if they are used over a long time period, systemic side effects, involving the functional suppression of the hypothalamus, the hypophysis and the adrenocortex are produced.

Despite that fact that they are used as external preparations, they additionally often bring about local side effects in the form of skin symptoms, such as for example deterioration of skin infections and acne characteristics of adrenocortical hormones. In the course of administration, reference is likewise being made to scars, liver spots and freckles as well as to problems with regard to the reaction after administration has finished.

On account of the above problems, immunosuppressives, antihistamines and antiallergics etc. have been developed as therapeutic agents for atopic dermatitis. However, immunosuppressives involve problems, such as e.g. a deterioration of bacterial skin infections, and antihistamines involve problems of disadvantageous side effects, such as e.g. medicament rash.

With regard to atopic dermatitis, a cause which has hitherto still not been identified, patients suffer with symptoms, and their family members also suffer with itching. Skin itching or pruritus is a widespread dermatological symptom which can be the cause of considerable impairments both in people and in animals Pruritus is often associated with inflammatory skin diseases by oversensitivity reactions.

Existing treatments which have been used for treating pruritus involve the use of corticosteroids and antihistamines. However, the occurrence of undesired side effects is known for both of these treatments. Other therapies which have been used involve the use of food supplements with essential fatty acids although these are associated with the disadvantages of being slow-acting and of offering only limited efficacy towards allergic dermatitis. A large number of softening agents, such as for example spreadable paraffin, glycerol and lanolin, are likewise used, but with limited success.

There is therefore a continuing need for alternative and/or improved treatment for skin itching (pruritus).

Since definitive treatment methods hitherto have still not been established by healthcare institutes, for example universities, hospitals etc., there is an urgent need for the development of an effective external preparation for a therapeutic or prophylactic treatment of atopic dermatitis which is as free as possible from side effects in order to replace the steroid-type-antiinflammatory external preparations.

The TRP channels (transient receptor potential channels) are a comprehensive family of cellular ion channels which can be divided into seven subfamilies. The homology (DNA or amino acid sequence relationship) between the subfamilies is only moderately pronounced. A common feature of all of the members is that they have 6 transmembrane regions and are permeable for cations.

A distinction is made between the following subfamilies:

Classic subfamily (TRPC)

Vanilloid receptor subfamily (TRPV)

Melastatin subfamily (TRPM)

NOMPC subfamily (TRPN)

ANKTM1 subfamily (TRPA)

Mucolipin subfamily (TRPML)

Polycystin subfamily (TRPP)

It is assumed that in each case four protein subunits in the cell membrane form an ion channel with a central pore (tetramer). Both homotetramers (four identical subunits) and heterotetramers (tetramers of two or more different subunits) are possible.

TRP channels are evolutionarily very old (they can be found e.g. as early as in yeast cells). The function of most TRP channels, however, is still largely unexplained. Insects, for example, require TRP channels for vision and for perceiving pain.

In humans, TRP channels play an important role in the perception of taste (sweet, sour, umami), pheromones, temperature (warm, hot, cold), pain etc.

The TRPM-8 receptor for example is also known as "cold and menthol receptor 1", also CMR1, i.e. cold-and-menthol-receptor. Agonists for the TRPM-8 receptor, for example linalool, geraniol, hydroxycitronellal, WS-3 (N-ethyl-p-menthane-3-carboxamide, WS-23 (2-isopropyl-N,2,3-trimethylbutyramide), Frescolat MAG (1,4-dioxaspiro[4.5]decane-2-methanol), Frescolat ML (menthyl lactate), Coolact P (5-methyl-2-prop-1-en-2-ylcyclohexan-1-ol) and Cooling Agent 10 (menthoxypropanediol) bring about a cold feel.

SUMMARY OF THE INVENTION

It was consequently surprising and unforeseeable by the person skilled in the art that agonists for the TRPM-8 receptor, in particular one or more substances selected from the group for example linalool, geraniol, hydroxycitronellal, WS-3 (N-ethyl-p-menthane-3-carboxamide, WS-23 (2-isopropyl-N,2,3-trimethylbutyramide), Frescolat MAG (1,4-dioxaspiro[4.5]decane-2-methanol), Frescolat ML (menthyl lactate), Coolact P (5-methyl-2-prop-1-en-2-ylcyclohexan-1-ol) and Cooling Agent 10 (menthoxypropanediol), are suitable for use as medicaments to counter atopic dermatitis and would solve the problems of the prior art.

A preferred TRPM-8 agonist according to the invention is Cooling Agent 10 (menthoxypropanediol) with the structure

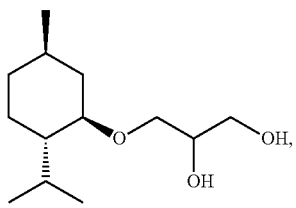 [SMILES: CC(C)[C@@H]1CC[C@@H](C)C[C@H]1OCC(O)CO]

According to the invention, the TRPM-8 agonists used according to the invention are preferably used in cosmetic or dermatological compositions a content of 0.005-50.0% by weight, in particular 0.01-20.0% by weight, based on the total weight of the composition are preferred. Advantageously, the compositions comprise 0.02-10.0% by weight, particularly preferably 0.02-5.0% by weight, very particularly advantageously 0.3-3.0% by weight, in each case based on the total weight of the composition.

It is of great advantage in the context of the invention if antimicrobially effective (in particular antibacterially effective) substances and/or antierythematos and/or antiinflammatory substances are added to the preparations in accordance with the invention.

In the context of the present invention, one or more substances from the group of polyols can for example be selected advantageously as antimicrobially effective substance or substances.

According to the invention, the polyols can advantageously be selected from the group of at least bifunctional alcohols. Advantageously, the polyols are in particular selected from the group below:
ethylene glycol, polyethylene glycols with molar masses up to about 2,000, propylene glycol-1,2, polypropylene glycols-1,2 with molar masses up to about 2,000, propylene glycol-1,3, polypropylene glycols-1,3 with molar masses up to about 2,000, butylene glycol-1,2, polybutylene glycols-1,2 with molar masses up to about 2,000, butylene glycol-1,3, polybutylene glycols-1,3 with molar masses up to about 2,000, butylene glycol-1,4, polybutylene glycols-1,4 with molar masses up to about 2,000, butylene glycol-2,3, polybutylene glycols-2,3 with molar masses up to about 2,000, α,ω-alkanediols, glycerol, diglycerol, triglycerol, tetraglycerol and pentaglycerol, where the oligoglycerols, and fatty acid esters thereof are composed of glycerol units condensed via one or more ether bridges, for example as follows:

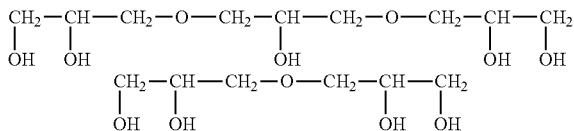

Very preferred polyols are selected from the group of vicinal diols, i.e. the 1,2-alkanediols. Among these, preference is in turn given to 1,2-pentanediol, 1,2-hexanediol. 1,2-heptanediol, 1,2-octanediol. 1,2-nonanediol and 1,2-decanediol.

According to the invention, the polyol or polyols used according to the invention are preferably used in cosmetic or dermatological compositions a content of 0.005-50.0% by weight, in particular 0.01-20.0% by weight, based on the total weight of the composition are preferred. Advantageously, the compositions comprise 0.02-10.0% by weight, particularly preferably 0.02-5.0% by weight, of one or more polyols used according to the invention, very particularly advantageously 0.3-3.0% by weight, in each case based on the total weight of the composition.

Advantageous anti-erythematos or anti-inflammatory active ingredients in the context of the present invention are, for example, licochalcone A, lignin, chroman- and isoflavonoids, pentacyclic triterpenes (e.g. ursolic acid, glycyrrhetic acid), hamamelis chamomile extracts or bisabolol, allantoin, calendula extracts and/or panthenol.

Licochalcone A is characterized by the following structural formula:

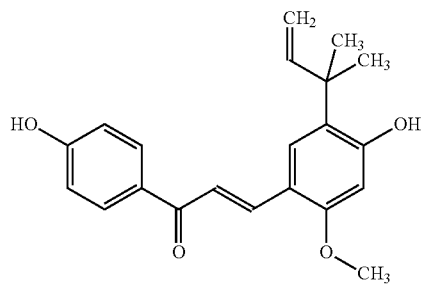 [SMILES: C=CC(C)(C)c1cc(/C=C/C(=O)c2ccc(O)cc2)c(OC)cc1O]

It is obtained in the form of aqueous extracts from the root of the plant species *Glycyrrhiza inflata* which, like the liquorice *Glycyrrhiza glabra* officinal in Europe, belongs to the genus *Glycyrrhiz*, which in turn belongs to the Fabaceae plant family (pea plants). The drug Radix *Glycyrrhizae inflatae*, i.e. the root of the plant, is used widely, for example in far eastern medicine. Use of the drug as antiinflammatory is likewise known.

According to the invention the anti-inflammatory active ingredient or ingredients used according to the invention are preferably used in cosmetic or dermatological compositions a content of 0.005-50.0% by weight, in particular 0.01-20.0% by weight, based on the total weight of the composition are preferred. Advantageously, the compositions comprise 0.02-10.0% by weight, particularly preferably 0.02-5.0% by weight, of one or more anti-inflammatory active ingredients used according to the invention, very particularly advantageously 0.3-3.0% by weight, in each case based on the total weight of the composition.

The active ingredient used according to the invention can advantageously be incorporated into customary cosmetic and dermatological preparations, which can be present in various forms. Thus, they can be e.g. a solution, an emulsion of the water-in-oil (W/O) type or of the oil-in-water (O/W) type, or multiple emulsions, for example of the water-in-oil-in-water (W/O/W) type or oil-in-water-in-oil (O/W/O) type, a hydrodispersion or lipodispersion, a Pickering emulsion, a gel, a solid stick or else an aerosol.

Emulsions according to the invention in the context of the present invention, e.g. in the form of a cream, lotion, cosmetic milk are advantageous and comprise e.g. fats, oils, waxes and/or other fatty bodies, as well as water and one or more emulsifiers, as are customarily used for such a type of formulation.

It is also possible and advantageous in the context of the present invention to add the active ingredient used according to the invention to aqueous systems and/or surfactant preparations for cleansing the skin and the hair.

Of course, it is known to the person skilled in the art that high-performance cosmetic compositions are in most cases inconceivable without the customary auxiliaries and additives. These include, for example, consistency regulators, fillers, perfume, dyes, emulsifiers, additional active ingredients such as vitamins or proteins, light protection agents, stabilizers, insect repellents, alcohol, water, salts, antimicrobial, proteolytic or keratolytic substances etc.

Corresponding requirements apply mutatis mutandis to the formulation of medicinal preparations.

Medicinal topical compositions in the context of the present invention generally comprise one or more medicaments in an effective concentration. For the sake of simplicity, for a clear distinction between cosmetic and medicinal application and corresponding products, reference is made to the legal provisions of the Federal Republic of Germany (e.g. Cosmetics Ordnance, Food and Drugs Act).

In this connection, it is likewise advantageous to add the active ingredient used according to the invention as additive to preparations which already comprise other active ingredients for different purposes.

Accordingly, cosmetic or topical dermatological compositions in the context of the present invention can, depending on their composition, for example, be used as skin protection cream, cleansing milk, sunscreen lotion, nutrient cream, day or night cream etc. It is likewise possible and advantageous to use the compositions according to the invention as a basis for pharmaceutical formulations.

For application, the cosmetic and dermatological preparations are applied in accordance with the invention to the skin and/or the hair in adequate amount in the manner customary for cosmetics.

Particular preference is given to those cosmetic and dermatological preparations which are in the form of a sunscreen composition. Advantageously, these can additionally comprise at least one further UVA filter and/or at least one further UVB filter and/or at least one inorganic pigment, preferably an inorganic micropigment.

According to the invention, the cosmetic and dermatological preparations can comprise cosmetic auxiliaries, as are customarily used in such preparations, e.g. preservatives, bactericides, perfumes, substances for preventing foaming, dyes, pigments which have a coloring effect, thickeners, moisturizing and/or humectants substances, fats, oils, waxes or other customary constituents of a cosmetic or dermatological formulation such as alcohols, polyols, polymers, foam stabilizers, electrolytes, organic solvents or silicone derivatives.

An additional content of customary antioxidants is generally preferred. According to the invention, favorable antioxidants that can be used are all antioxidants that are suitable or customary for cosmetic and/or dermatological applications.

The amount of the aforementioned antioxidants (one or more compounds) in the preparations is preferably 0.001 to 30% by weight, particularly preferably 0.05-20% by weight, in particular 1-10% by weight, based on the total weight of the preparation.

If the cosmetic or dermatological preparation in the context of the present invention is a solution or emulsion or dispersion, solvents that can be used are:
water or aqueous solutions
oils, such as triglycerides of capric acid or of caprylic acid, but preferably castor oil;
fats, waxes and other natural and synthetic fatty bodies, preferably esters of fatty acids with alcohols of low carbon number, e.g. with isopropanol, propylene glycol or glycerol, or esters of fatty alcohols with alkanoic acids of low carbon number or with fatty acids;
alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the aforementioned solvents are used. In the case of alcoholic solvent, water can be a further constituent.

In particular, mixtures of the aforementioned solvents are used. In the case of alcoholic solvents, water can be a further constituent.

In the context of the present invention, suitable propellants for cosmetic and/or dermatological preparations that can be sprayed from aerosol containers are the customary known readily volatile, liquefied propellants, for example hydrocarbons (propane, butane, isobutane), which can be used on their own or in a mixture with one another. Compressed air can also advantageously be used.

The person skilled in the art is, of course, aware that there are propellant gases that are nontoxic per se which would be suitable in principle for realizing the present invention in the form of aerosol preparations, but which nevertheless should be avoided on account of an unacceptable impact on the environment or other surrounding circumstances, in particular fluorocarbons and chlorofluorocarbons (CFCs).

Cosmetic preparations in the context of the present invention can also be in the form of gels which, besides an effective content of the active ingredient according to the invention and solvents customarily used for this purpose, preferably comprise water, further organic thickeners, e.g. gum arabic, xanthan gum, sodium alginate, cellulose derivatives, preferably methylcellulose, hydroxymethylcellulose, hydroxyethylcellulose, hydroxypropylcellulose, hydroxypropyl-methylcellulose or inorganic thickeners, e.g. aluminum silicates such as, for example, bentonites, or a mixture of polyethylene glycol and polyethylene glycol stearate or distearate. The thickener is present in the gel e.g. in an amount between 0.1 and 30% by weight, preferably between 0.5 and 15% by weight.

It is advantageous according to the invention to use, apart from the combinations according to the invention, further oil-soluble UVA filters and/or UVB filters in the lipid phase and/or further water-soluble UVA filters and/or UVB filters in the aqueous phase.

Advantageously, the light protection formulations can according to the invention comprise further substances which absorb UV radiation in the UVB region, with the total amount of the filter substances being e.g. 0.1% by weight to 30% by weight, preferably 0.5 to 10% by weight, in particular 1 to 6% by weight, based on the total weight of the preparations, in order to provide cosmetic preparations which protect the skin against the entire range of ultraviolet radiation. It can also serve as sunscreen compositions.

DEMONSTRATION OF EFFECT

The aim of the present study was the investigation of the effectiveness of an optimized skin care formula consisting of licochalcone A (*Glycyrrhiza Inflata* wheat extract), decanediol, Cooling Agent 1 (Coolant XL) and Cooling Agent 10 (Coolact CA10) as anti-inflammatory, antibacterial and anti-pruritogenic substances on patients with atopic dermatitis of mild to moderate severity.

Using a randomized, blind (participant), controlled, two-armed study design, it was the aim to evaluate the cortisone saving potential and the non-inferiority of the test sample during an application twice daily lasting for four weeks compared to the once-weekly treatment with 1% hydrocortisone (HC), followed by an application of the test sample for a further three weeks. The study results were based on an assessment, controlled by the dermatologist, of the degree of severity of the clinical size of atopic dermatitis, the colonization of the skin lesions with S. aureus, biotechnological measurement of parameters of the epidermal barrier function, as well as the itching intensity in the test area.

The results of the study provide prove for the fact that the aims defined in the study protocol have been achieved. Similarly to 1% hydrocortisone, the single application of the test sample exhibited a significant reduction in local SCORAD, erythema, lesional skin TEWL (transepidermal water loss), and also a significant reduction in the colonization of skin lesions with S. aureus. Whereas the application of 1% HC within the first study week induced greater changes in the aforementioned parameters, apart from TEWL on day 7 for lesional skin, there were at no time significant differences between the investigated arms.

It should be emphasized in particular that the reduction in local SCORAD, lesional skin TEWL, erythema and S. aureus colonization, determined as a percentage change compared to the starting value on the corresponding arm A and arm B, were comparable at the end of the study. It can be concluded from this that a non-inferiority of the sole application of the test sample is present compared to a treatment approach with 1% hydrocortisone and the test sample. This result shows a potential cortisone-saving effect of the test sample, which corresponds to the amount of topical steroid used per patient in the first study week (6.08 g 1% HC/7 days).

The application of the test sample or 1% HC in the first study week resulted in differences as regards the effects exerted on skin moisturization. Whereas the application of 1% HC wetted the lesional skin only slightly, the application of the test sample 37175-10 achieved a significant increase in skin moisture on the particular test arm. It is important to note that the increase in lesional skin moisture at the end of the study was significant for both test arms A and B, which suggests the conclusion that the observed increase in skin moisture following the discontinuous application of 1% HC on the respective test arm is to be attributed to the use of the test sample 37175-10. The test sample was generally readily skin-compatible. The subjective assessment mentioned most often following application of the test samples was a burning, which was felt by 16.7% of the subjects irrespective of the test arm and time point. Skin reddening, crust formation, skin dryness, skin tension or other subjective assessments were only mentioned in isolated cases.

The study results accordingly show that the twice daily application of the test sample 37175-10 constitutes, as a result of a reduction in the clinical severity (local SCORAD), an improvement in skin barrier parameters, a reduction in pathogenic bacterial colonization, and a measurable cortisone saving potential, an essential benefit for the treatment of acute-eczematous lesions of patients with mild to moderate atopic dermatitis.

DETAILED DESCRIPTION OF THE INVENTION

The examples below serve to illustrate the present invention without limiting it. Unless stated otherwise, all amounts, fractions and percentages are based on the weight and the total amount or on the total weight of the preparations.

| | Formulation examples | | | |
|---|---|---|---|---|
| | 1 | 2 | 3 | 4 |
| INCI name | % by weight | % by weight | % by weight | % by weight |
| Stearic Acid | 2.5 | 2.0 | 2.0 | 2.5 |
| Glyceryl Stearate | 1.0 | 1.0 | 1.0 | 1.0 |
| C12-15 Alkyl Benzoate | 3.0 | 5.00 | 3.0 | 2.0 |
| Caprylic Acid/Capric Acid Triglycerides | 2.5 | 2.50 | 2.0 | 2.5 |
| Isopropyl Palmitate | 2.0 | — | — | 2.0 |
| Cetylstearyl Alcohol | 3.0 | — | 2.0 | 3.0 |
| Cetyl Alcohol | — | 2.00 | — | — |
| Stearyl Alcohol | — | 2.00 | 1.0 | — |
| Cyclomethicone | 1.0 | 1.0 | 0.5 | — |
| Dicaprylyl Carbonate | 2.0 | 2.00 | 2.00 | 2.0 |
| Dimethicone | 1.0 | — | 0.5 | 1.0 |
| Glycerol | 5 | 7.0 | 5.0 | 9.0 |
| Methylparaben | 0.2 | — | — | — |
| Phenoxyethanol | 0.4 | 0.50 | 0.5 | 0.4 |
| Propylparaben | 0.1 | — | — | 0.1 |
| 1,2-Hexanediol | — | — | 0.1 | 0.1 |
| Ethylhexylglycerol | — | — | 0.2 | — |
| Methylisothiazolinone | — | 0.05 | — | — |
| Butylene glycol | — | — | 2.0 | — |
| Carbomer | 0.15 | 0.10 | 0.15 | 0.1 |
| Carrageenan | 0.10 | — | 0.10 | — |
| Xanthan Gum | — | — | 0.10 | — |
| Acrylates/C10-30 Alkyl Acrylate Crosspolymer | — | 0.10 | — | 0.1 |
| Trisodium EDTA | 0.20 | 0.20 | 0.2 | 0.2 |
| Tapioca Starch | 1.5 | 1.0 | — | — |
| Nylon-12 | — | 0.2 | — | 0.5 |
| Polymethylsissesquioxane | — | 1.00 | 1.0 | — |
| Aluminum Starch Octenylsuccinate | — | — | 1.0 | — |
| Distarch Phosphate | 1.0 | — | — | 1.0 |
| Butyl Methoxydibenzoylmethane | 1.00 | 2.00 | 1.00 | 1.00 |
| Phenylbenzimidazole Sulfonic Acid | — | 1.00 | 2.00 | — |
| Octocrylene | — | 2.00 | 1.00 | — |
| Ethylhexyl Salicylate | 1.00 | — | — | 1.00 |
| 3-(Menthoxy)propane-1,2-diol | 0.001 | — | 1.00 | 0.10 |
| (1R,2S,5R)-N-(2-(2-Pyridinyl)ethyl)-2-ispropyl-5-methyl-cyclohexane-carboxamide | 0.10 | 0.030 | — | 0.30 |
| 1,2-Decanediol | 0.30 | 0.30 | 0.30 | 0.10 |
| Glycyrrhiza Inflata Root Extract | 0.025 | 0.05 | 0.05 | 0.025 |
| Sodium Hydroxide | q.s. | q.s. | q.s. | q.s. |
| Hydroxyisohexyl 3-cyclohexenecarboxaldehyde | 0.1 | — | — | 0.05 |
| Citronellol | 0.05 | 0.1 | — | 0.05 |
| Linalool | — | 0.05 | 0.1 | — |
| Perfume | 0.3 | 0.2 | 0.2 | 0.2 |
| Sodium Hydroxide | q.s. | q.s. | q.s. | q.s. |
| Water | ad 100 | ad 100 | ad 100 | ad 100 |

| | Formulation examples | | | |
|---|---|---|---|---|
| | 5 | 6 | 7 | 8 |
| INCI name | % by weight | % by weight | % by weight | % by weight |
| Glyceryl Stearate Citrate | 2.0 | 1.5 | 2.0 | 2.0 |
| Behenyl Alcohol | 1.5 | 1.0 | 1.0 | 1.0 |
| C12-15 Alkyl Benzoate | 2.0 | 2.5 | 2.0 | 2.5 |
| Caprylic Acid/Capric Acid Triglyceride | 2.0 | 2.0 | 2.5 | 2.5 |
| Cetyl Alcohol | 2.0 | 2.0 | — | 2.0 |
| Cetylstearyl Alcohol | — | — | 2.0 | — |
| Cyclomethicone | 1.0 | 1.0 | 2.0 | 2.0 |
| Dicaprylyl Carbonate | — | 2.0 | 2.5 | 2.5 |
| Paraffinum Liquidum | — | — | 0.5 | — |
| Octyldodecanol | — | 2.0 | — | — |
| Dimethicone | 0.5 | 1.00 | 1.00 | — |
| Glycerol | 3.00 | 5.00 | 7.00 | 9.00 |
| Methylparaben | 0.20 | 0.15 | — | — |

-continued

| INCI name | Formulation examples | | | |
|---|---|---|---|---|
| | 5 % by weight | 6 % by weight | 7 % by weight | 8 % by weight |
| Phenoxyethanol | 0.40 | 0.60 | 0.5 | 0.50 |
| Propylparaben | 0.10 | — | — | — |
| Methylisothiazolinone | — | — | 0.05 | — |
| Piroctone Olamine | — | — | — | 0.15 |
| Glyceryl Caprylate | — | — | — | 0.2 |
| Carbomer | 0.20 | — | 0.15 | 0.15 |
| Sodium Polyacrylate | — | 0.4 | — | — |
| Xanthan Gum | 0.10 | — | 0.10 | — |
| Acrylates/C10-30 Alkyl Acrylate Crosspolymer | — | 0.1 | — | 0.1 |
| Tapioca Starch | 0.50 | — | 0.50 | — |
| Nylon-12 | 1.0 | — | — | 1.0 |
| Polymethylsilsesquioxane | — | 1.0 | 1.0 | — |
| Aluminum starch Octenylsuccinate | — | 1.0 | — | 1.00 |
| 3-(Menthoxy)propane-1,2-diol | 0.01 | — | 1.0 | 0.10 |
| (1R,2S,5R)-N-(2-(2-Pyridinyl)eth-yl)-2-ispropyl-5-methyl-cyclohexane-carboxamide | 0.20 | 0.10 | — | 0.30 |
| 1,2-Decanediol | 0.10 | 0.20 | 0.30 | 0.20 |
| *Glycyrrhiza Inflata* Root Extract | 0.025 | 0.05 | 0.05 | 0.03 |
| Titanium Dioxide | — | 1.0 | — | — |
| Octocrylene | — | 1.0 | — | 2.0 |
| Bis-Ethylhexyloxyphenol Methoxyphenyl Triazines | — | 1.0 | 1.0 | — |
| 2-Ethylhexyl Methoxycinnamate | — | 1.0 | 2.0 | 2.0 |
| Homosalate (3,3,5-trimethylcyclohexyl salicylate) | — | — | 1.0 | 1.0 |
| Sodium Hydroxide | q.s. | q.s. | q.s. | q.s. |
| 1-(1,2,3,4,5,6,7,8-Octahydro-2,3,8,8-tetramethyl-2-naphthyl)ethan-1-one | 0.1 | — | q.s. | q.s. |
| Geraniol | — | 0.05 | — | — |
| Hexylcinnamal | — | — | 0.05 | — |
| Perfume | 0.1 | 0.2 | 0.3 | 0.2 |
| Water | ad 100 | ad 100 | ad 100 | ad 100 |

| INCI name | Formulation examples | | | |
|---|---|---|---|---|
| | 9 % by weight | 10 % by weight | 11 % by weight | 12 % by weight |
| Polyglyceryl-3 Methylglucose Distearate | 2.00 | 2.50 | 2.50 | 2.50 |
| Sorbitan Stearate | 1.50 | 3.00 | 1.50 | 3.00 |
| C12-15 Alkyl Benzoate | 2.50 | 2.50 | 2.50 | 2.50 |
| Caprylic Acid/Capric Acid Triglycerides | 2.50 | 2.50 | 2.50 | 2.50 |
| Stearyl Alcohol | 1.00 | 1.50 | 1.00 | 1.50 |
| Cyclomethicone | 3.00 | 1.00 | 2.00 | 1.00 |
| Isopropyl Myristate | — | 2.50 | 2.0 | 2.50 |
| Isopropyl Palmitate | 2.0 | — | 1.0 | — |
| Dimethicone | — | 1.00 | — | 1.00 |
| Glycerol | 5.00 | 7.50 | 3.00 | 7.50 |
| *Butyrospermum Parkii* Butter | 2.0 | — | — | — |
| Methylparaben | 0.20 | 0.20 | — | 0.1 |
| Phenoxyethanol | 0.40 | 0.40 | 0.40 | 0.40 |
| Propylparaben | 0.10 | — | — | — |
| Benzethonium Chloride | — | — | 0.1 | — |
| Caprylyl Glycol | — | 0.2 | — | — |
| Ethylhexylglycerol | — | 0.2 | — | 0.2 |
| Carbomer | 0.15 | 0.10 | 0.15 | 0.10 |
| Ammonium Acryloyldimethyltaurate/VP Copolymer | — | 0.2 | — | 0.2 |
| Carrageenan | 0.1 | — | 0.15 | — |
| Trisodium EDTA | — | 1.00 | — | 1.00 |
| Tapioca Starch | — | 1.00 | 1.0 | — |
| Distarch Phosphate | — | 1.00 | — | 1.0 |
| Acrylonitrile-methacrylonitrile-methyl-methacrylate Copolymer + Isopentane + Magnesium Hydroxide | — | — | 1.0 | 1.0 |
| 3-(Menthoxy)propane-1,2-diol | 0.05 | 1.0 | — | 0.10 |
| (1R,2S,5R)-N-(2-(2-Pyridinyl)eth-yl)-2-ispropyl-5-methyl-cyclohexane-carboxamide | 0.20 | 0.10 | 0.10 | 0.30 |
| 1,2-Decanediol | 0.30 | 0.30 | 0.30 | 0.30 |
| *Glycyrrhiza Inflata* Root Extract | 0.025 | 0.05 | 0.05 | 0.03 |
| Diethylamino Hydroxybenzoyl Hexyl Benzoate | — | — | 1.0 | — |
| Ethylhexyl Methoxycinnamate | — | 1.00 | — | 2.00 |
| Butyl Methoxydibenzoylmethane | — | 2.00 | — | 2.00 |
| Octocrylene | — | 1.00 | 2.0 | 1.00 |
| Titanium Dioxide | — | — | 1.0 | — |
| Sodium Hydroxide | q.s. | q.s. | q.s. | q.s. |
| Sodium Metabisulfite | — | 0.15 | — | — |
| BHT (tert-Butylhydroxytoluene) | — | — | 0.05 | — |
| Linalyl Acetate | 0.05 | — | — | — |
| Hexyl Salicylate | — | 0.05 | — | — |
| Benzyl Salicylate | — | — | 0.01 | — |
| Perfume | q.s. | q.s. | q.s. | q.s. |
| Water | ad 100 | ad 100 | ad 100 | ad 100 |

| INCI name | Formulation examples | | | |
|---|---|---|---|---|
| | 13 % by weight | 14 % by weight | 15 % by weight | 16 % by weight |
| PEG-40 Stearate | 0.80 | 1.00 | 1.00 | 1.00 |
| Glyceryl Stearate | 2.50 | 3.00 | 3.00 | 3.00 |
| C12-15 Alkyl Benzoate | 2.00 | 2.50 | 2.00 | 2.00 |
| Caprylic Acid/Capric Acid Triglycerides | 2.00 | 2.50 | 2.50 | 2.00 |
| Cetylstearyl Alcohol | 3.00 | 3.00 | 3.00 | 3.00 |
| Cyclomethicone | 2.00 | 2.00 | 2.00 | 2.00 |
| Dicaprylyl Carbonate | — | 2.00 | 2.50 | 2.50 |
| Octyldodecanol | 1.0 | — | — | 1.50 |
| *Butyrospermum Parkii* Butter | 2.0 | — | — | — |
| Octyldodecyl Myristate | 1.0 | — | 1.5 | 1.0 |
| Dimethicone | 1.00 | 1.00 | 1.00 | 1.00 |
| Glycerin | 7.50 | 5.0 | 9.0 | 7.50 |
| Methylparaben | 0.20 | — | 0.1 | — |
| Phenoxyethanol | 0.40 | 0.50 | 0.40 | 0.40 |
| Propylparaben | 0.10 | — | — | — |
| Glyceryl Caprylate | — | 0.25 | — | — |
| Pentylene Glycol | — | 0.5 | — | — |
| Butylene Glycol | — | — | 3.0 | — |
| Carbomer | 0.15 | 0.10 | 0.10 | 0.15 |
| Sodium Polyacrylate | — | 0.20 | 0.20 | — |
| Xanthan Gum | 0.10 | — | — | — |
| Acrylates/C10-30 Alkyl Acrylate Crosspolymer | — | — | — | 0.1 |
| Trisodium EDTA + Water (20% strength solution) | — | 1.00 | 1.00 | 1.00 |
| Tapioca Starch | — | 1.00 | 1.00 | 1.00 |
| Distarch phosphate | — | 1.00 | 1.00 | 1.00 |
| Aluminum Starch Octenylsuccinate | 2.0 | — | — | — |
| Acrylonitrile-methacrylonitrile-methyl-methacrylate Copolymer + Isopentane + Magnesium Hydroxide | 1.0 | — | — | — |
| 3-(Menthoxy)propane-1,2-diol | 0.05 | 0.10 | — | 0.10 |
| (1R,2S,5R)-N-(2-(2-Pyridinyl)eth-yl)-2-ispropyl-5-methyl-cyclohexane-carboxamide | 0.20 | — | 0.10 | 0.30 |

-continued

| INCI name | Formulation examples | | | |
|---|---|---|---|---|
| | 13 % by weight | 14 % by weight | 15 % by weight | 16 % by weight |
| 1,2-Decanediol | 0.30 | 0.30 | 0.30 | 0.30 |
| Glycyrrhiza Inflata Root Extract | 0.025 | 0.05 | 0.05 | 0.03 |
| Ethylhexyl Methoxycinnamate | — | 1.00 | 1.00 | 2.00 |
| Diethylamino Hydroxybenzoyl Hexyl Benzoate | — | 1.00 | — | 1.00 |
| Titanium Dioxide | — | — | 1.0 | — |
| Homosalate (3,3,5-trimethylcyclohexyl salicylate) | — | — | 2.0 | — |
| Phenylbenzimidazole Sulfonic Acid | — | — | 1.0 | — |
| Sodium hydroxide | q.s. | q.s. | q.s. | q.s. |
| 3-Methyl-5-phenyl-1-pentanol | 0.1 | — | — | — |
| Coumarin | — | 0.05 | — | — |
| Ethyllinalool | — | — | 0.1 | — |
| Perfume | q.s. | q.s. | q.s. | q.s. |
| Water | ad 100 | ad 100 | ad 100 | ad 100 |

| INCI name | Formulation examples | | | |
|---|---|---|---|---|
| | 17 % by weight | 18 % by weight | 19 % by weight | 20 % by weight |
| PEG-40 Stearate | 1.00 | 1.00 | 1.00 | 1.00 |
| Glyceryl Stearate | 2.00 | 2.50 | 2.50 | 2.00 |
| C12-15 Alkyl Benzoate | — | — | 1.00 | — |
| Caprylic Acid/Capric Acid Triglycerides | 6.00 | 4.00 | 5.00 | 6.00 |
| Glyceryl Caprylate | — | 1.00 | 0.50 | — |
| Cetyl Alcohol | 2.00 | 3.00 | 2.00 | 2.00 |
| Cyclomethicone | 3.00 | 2.50 | 2.50 | 3.00 |
| Pentaerythrityl Tetraisostearate | 4.00 | 3.00 | 4.50 | 4.00 |
| Triisostearin | 3.00 | 4.00 | 3.50 | 3.00 |
| Oenothera Biennis Oil (evening primrose oil) | 3.00 | 2.00 | 2.00 | 3.00 |
| Vitis Vinifera Seed Oil (grape seed oil) | 3.00 | 4.00 | 4.00 | 3.00 |
| Ceramide III | 0.05 | 0.10 | 0.1 | 0.05 |
| Dimethicone | 5.00 | 3.00 | 4.00 | 5.00 |
| Glycerol | 10.00 | 8.00 | 9.00 | 10.00 |
| Pirctone Olamine | 0.10 | 0.05 | 0.15 | 0.10 |
| Phenoxyethanol | 0.20 | 0.40 | 0.30 | 0.20 |
| 1,2-Hexanediol | 0.50 | — | 0.30 | 0.50 |
| 1,2-Decanediol | 0.20 | 0.25 | 0.30 | 0.20 |
| BHT (tert-Butylhydroxytoluene) | 0.05 | 0.05 | 0.05 | 0.05 |
| Trisodium EDTA + Water (20% strength aqueous solution) | 0.50 | 1.00 | 1.00 | 0.50 |
| 3-(Menthoxy)propane-1,2-diol | 0.05 | 0.10 | — | 0.10 |
| (1R,2S,5R)-N-(2-(2-Pyridinyl)ethyl)-2-ispropyl-5-methylcyclohexane-carboxamide | 0.20 | — | 0.10 | 0.30 |
| 1,2-Decanediol | 0.30 | 0.30 | 0.30 | 0.20 |
| Glycyrrhiza Inflata Root Extract | 0.025 | 0.05 | 0.05 | 0.03 |
| Menthoxypropanediol | 0.10 | 0.15 | 0.20 | 0.10 |
| (1R,2S,5R)-N-(2-(2-Pyridinyl)ethyl)-2-ispropyl-5-methyl-cyclohexane-carboxamide | 0.05 | 0.10 | 0.20 | 0.10 |
| 1-(1,2,3,4,5,6,7,8-Octahydro-2,3,8,8-tetramethyl-2-naphthyl)ethan-1-one | — | 0.05 | 0.10 | — |
| Sodium Citrate | 0.20 | 0.15 | 0.15 | 0.20 |
| Citric Acid | q.s. | q.s. | q.s. | q.s. |
| Xanthan Gum | — | — | 0.10 | — |
| Water | ad 100 | ad 100 | ad 100 | ad 100 |

| INCI name | Formulation examples | | | |
|---|---|---|---|---|
| | 21 % by weight | 22 % by weight | 23 % by weight | 24 % by weight |
| Glyceryl Stearate Citrate | 2.0 | 2.0 | 2.0 | 2.0 |
| Isopropyl Palmitate | 3.0 | 2.0 | 3.0 | 1.0 |
| Cetylstearyl Alcohol | 4.0 | 3.0 | 3.0 | — |
| Cetyl Alcohol | — | — | — | 4.0 |
| Caprylic Acid/Capric Acid Triglycerides | 3.0 | 2.5 | 2.0 | 3.0 |
| C12-15 Alkyl Benzoate | 3.0 | 2.5 | 2.0 | 2.0 |
| Cyclomethicone | 1.0 | — | 1.0 | — |
| Dicaprylyl Carbonate | — | — | 2.5 | — |
| Dimethicone | — | 0.50 | — | — |
| Octyldodecyl Myristate | — | 1.0 | — | — |
| Glycerol | 4.00 | 6.00 | 5.00 | 6.00 |
| Methylparaben | 0.20 | — | 0.10 | — |
| Phenoxyethanol | 0.40 | 0.40 | 0.40 | 0.40 |
| Piroctone Olamine | — | — | — | 0.10 |
| Ethylhexylglycerol | — | 0.3 | — | — |
| Glyceryl Caprylate | — | 0.3 | — | — |
| 2-Methyl-1,3-propanediol | — | 2.0 | — | 2.0 |
| Carbomer | 0.20 | 0.10 | 0.15 | — |
| Sodium Polyacrylate | — | 0.40 | — | — |
| Xanthan Gum | 0.10 | — | — | 0.15 |
| Acrylates/C10-30 Alkyl Acrylate Crosspolymer | — | — | 0.1 | 0.2 |
| Acrylonitrile-methacrylonitrile-methyl-methacrylate Copolymer + Isopentane + Magnesium Hydroxide | 0.50 | — | 0.50 | — |
| Aluminum Starch Octenylsuccinate | — | 1.00 | — | 1.00 |
| Methyl Methacrylate Crosspolymer | 1.0 | — | — | 1.0 |
| 3-(Menthoxy)propane-1,2-diol | — | 0.50 | 0.10 | 0.03 |
| (1R,2S,5R)-N-(2-(2-Pyridinyl)ethyl)-2-ispropyl-5-methylcyclohexane-carboxamide | 0.10 | — | 0.05 | 0.10 |
| 1,2-Decanediol | 0.30 | 0.30 | 0.30 | 0.30 |
| Glycyrrhiza Inflata Root Extract | 0.025 | 0.05 | 0.10 | 0.05 |
| Bis-Ethylhexyloxyphenol Methoxyphenyl Triazines | — | — | 1.0 | — |
| Titanium Dioxide | — | 1.00 | — | 1.00 |
| Octocrylene | — | 1.00 | 1.0 | 1.00 |
| Butyl Methoxydibenzoylmethane | — | 1.00 | — | 1.00 |
| Ethylhexyl Salicylate | — | — | 1.0 | — |
| Citronellol | 0.05 | — | 0.05 | — |
| Coumarin | 0.05 | 0.05 | — | 0.05 |
| Triethyl Citrate | — | — | 0.05 | 0.05 |
| Sodium Hydroxide | q.s. | q.s. | q.s. | q.s. |
| Water | ad 100 | ad 100 | ad 100 | ad 100 |

| INCI name | Formulation examples | | | |
|---|---|---|---|---|
| | 25 % by weight | 26 % by weight | 27 % by weight | 28 % by weight |
| Sucrose Polystearate + Hydrogenated Polyisobutene | 1.00 | 1.00 | 2.00 | 2.00 |
| Sodium Stearoyl Glutamate | 0.20 | 0.20 | 0.30 | 0.30 |
| C12-15 Alkyl Benzoate | 1.50 | 1.50 | — | — |
| Cetyl Alcohol | 0.50 | 0.50 | — | — |
| Cyclomethicone | 10.00 | 10.00 | 5.00 | 5.00 |
| Dimethicone | 3.00 | 3.00 | 2.50 | 2.50 |
| Glycerol | 7.50 | 7.50 | 5.00 | 5.00 |
| Isopropyl Stearate | 1.00 | 1.00 | 2.00 | 2.00 |
| Paraffinum Liquidum | 3.00 | 3.00 | 1.00 | 1.00 |
| Methylparaben | 0.10 | — | — | 0.10 |
| Ethylhexylglycerol | — | — | 0.3 | 0.10 |
| Propylparaben | 0.1 | — | — | — |

-continued

| INCI name | 25 % by weight | 26 % by weight | 27 % by weight | 28 % by weight |
|---|---|---|---|---|
| Methylisothiazolinone | — | 0.05 | — | — |
| Phenoxyethanol | 0.40 | 0.50 | 0.40 | 0.40 |
| 3-(Menthoxy)propane-1,2-diol | 0.05 | 0.50 | 0.10 | 0.05 |
| (1R,2S,5R)-N-(2-(2-Pyridinyl)eth-yl)-2-ispropyl-5-methylcyclohexane-carboxamide | 0.10 | 0.10 | 0.05 | 0.10 |
| 1,2-Decanediol | 0.30 | 0.30 | 0.30 | 0.30 |
| *Glycyrrhiza Inflata* Root Extract | 0.025 | 0.05 | 0.10 | 0.05 |
| Ethylhexyl Methoxycinnamate | 3.00 | 2.00 | 3.00 | 3.0 |
| Butyl Methoxydibenzoylmethane | 2.00 | 2.00 | 1.00 | 1.0 |
| Phenylbenzimidazole Sulfonic Acid | — | 1.5 | — | 1.0 |
| Butylene Glycol | — | — | 3.0 | — |
| Polymethylsissesquioxane | — | — | 1.0 | 1.0 |
| Nylon-12 | — | 1.0 | 1.0 | — |
| Distarch Phosphate | — | 1.0 | — | 1.0 |
| Methyl Methacrylate Crosspolymer | 1.0 | — | — | — |
| Aluminum Starch Octenylsuccinate | 1.0 | — | — | — |
| Ammonium Acryloyldimethyltaurate/VP Copolymer | — | — | 0.25 | 0.25 |
| Xanthan Gum | 0.10 | — | — | 0.1 |
| Acrylates/C10-30 Alkyl Acrylate Crosspolymer | 0.25 | 0.1 | — | — |
| Carbomer | — | 0.1 | 0.1 | — |
| Hexylcinnamal | 0.05 | 0.1 | — | 0.1 |
| 1-(1,2,3,4,5,6,7,8-Octahydro-2,3,8,8-tetramethyl-2-naphthyl)ethan-1-one | — | 0.1 | 0.1 | — |
| Linalool | — | — | 0.05 | 0.05 |
| Perfume | 0.2 | 0.2 | 0.2 | 0.2 |
| Sodium Hydroxide | q.s. | q.s. | q.s. | q.s. |
| Water | ad 100 | ad 100 | ad 100 | ad 100 |

| INCI name | 29 % by weight | 30 % by weight | 31 % by weight | 32 % by weight |
|---|---|---|---|---|
| Sodium Cetearyl Sulfate | 0.15 | 0.15 | 0.15 | 0.15 |
| Glyceryl Stearate SE | 2.00 | 2.00 | 1.50 | 1.50 |
| C12-15 Alkyl Benzoate | 2.50 | 2.50 | 2.50 | 2.50 |
| Octyldodecanol | 1.00 | 1.00 | — | — |
| Caprylic Acid/Capric Acid Triglycerides | 2.00 | 2.00 | 2.00 | 2.00 |
| Cetylstearyl Alcohol | 2.00 | 2.00 | 3.00 | 1.00 |
| Cyclomethicone | 1.50 | 1.50 | 2.50 | 2.50 |
| Dimethicone | 0.50 | 0.50 | 0.50 | 0.50 |
| Glycerol | 5.00 | 5.00 | 7.50 | 7.50 |
| Isopropyl Stearate | 3.00 | 3.00 | 2.00 | 2.00 |
| Paraffinum Liquidum | 2.00 | 2.00 | 1.00 | 1.00 |
| Methylisothiazolinone | — | — | — | 0.05 |
| Phenoxyethanol | 0.4 | 0.5 | 0.40 | 0.30 |
| Methylparaben | 0.15 | — | — | — |
| Propylparaben | 0.1 | — | — | — |
| Piroctone Olamine | — | 0.15 | — | — |
| Benzethonium Chloride | — | — | 0.10 | — |
| 3-(Menthoxy)propane-1,2-diol | — | 0.50 | 0.10 | 0.05 |
| (1R,2S,5R)-N-(2-(2-Pyridinyl)eth-yl)-2-ispropyl-5-methylcyclohexane-carboxamide | 0.10 | — | 0.05 | 0.10 |
| 1,2-Decanediol | 0.30 | 0.30 | 0.30 | 0.30 |
| *Glycyrrhiza Inflata* Root Extract | 0.025 | 0.05 | 0.10 | 0.05 |
| Ethylhexyl Methoxycinnamate | 3.00 | 3.00 | 5.00 | 5.00 |
| Butyl Methoxydibenzoylmethane | 1.00 | 1.00 | 2.00 | 2.00 |

-continued

| INCI name | 29 % by weight | 30 % by weight | 31 % by weight | 32 % by weight |
|---|---|---|---|---|
| Pentylene Glycol | — | 1.0 | 1.0 | — |
| Butylene Glycol | 1.0 | 1.5 | 3.0 | 3.0 |
| 2-Methyl-1,3-propanediol | — | — | — | — |
| 1,2-Hexanediol | — | — | — | 1.0 |
| Nylon-12 | 1.0 | 1.0 | 1.0 | 1.0 |
| Carbomer | — | — | 0.10 | 0.15 |
| Ammonium Acryloyldimethyltaurate/VP Copolymer | 0.20 | — | — | — |
| *Chondrus Crispus* | 0.10 | 0.10 | — | — |
| Xanthan Gum | — | — | 0.10 | — |
| Acrylates/C10-30 Alkyl Acrylate Crosspolymer | — | 0.2 | 0.1 | 0.1 |
| Coumarin | 0.1 | — | 0.05 | 0.05 |
| Hydroxyisohexyl 3-cyclohexenecarboxaldehyde | 0.05 | 0.05 | 0.05 | 0.1. |
| 1-(1,2,3,4,5,6,7,8-Octahydro-2,3,8,8-tetramethyl-2-naphthyl)ethan-1-one | — | 0.05 | 0.1 | — |
| Perfume | 0.2 | 0.3 | 0.4. | 0.2. |
| Sodium Hydroxide | q.s. | q.s. | q.s. | q.s. |
| Water | ad 100 | ad 100 | ad 100 | ad 100 |

| Chemical name | 33 % by weight | 34 % by weight | 35 % by weight | 36 % by weight |
|---|---|---|---|---|
| Sodium Cetearyl Sulfate | 0.15 | 0.15 | 0.2 | 0.2 |
| Glyceryl Stearate, self-emulsifying | 2 | 2 | 1.5 | 1.5 |
| C12-15 Alkyl Benzoate | 2 | 2 | 2 | 2 |
| Octyldodecanol | 1 | 1 | — | — |
| Caprylic Acid/Capric Acid Triglycerides | 2 | 2 | 2 | 2 |
| Cetylstearyl Alcohol | 2 | 2 | 1 | 1 |
| Cyclomethicone | 1 | 1 | 2 | 2 |
| Dimethicone | 0.5 | 0.5 | 1 | 1 |
| Glycerol | 5 | 5 | 7.5 | 7.5 |
| Isopropyl Palmitate | 2.5 | 2.5 | 2 | 2 |
| DMDM Hydantoin | 0.05 | 0.05 | 0.05 | 0.05 |
| Phenoxyethanol | 0.35 | 0.25 | 0.3 | 0.3 |
| Ethanol | — | — | 3.0 | 2.0 |
| Pentylene Glycol | 1.0 | — | 1.0 | 1.5 |
| 3-(Menthoxy)propane-1,2-diol | — | 0.50 | 0.10 | 0.05 |
| (1R,2S,5R)-N-(2-(2-Pyridinyl)eth-yl)-2-ispropyl-5-methyl-cyclohexane-carboxamide | 0.10 | — | 0.05 | 0.10 |
| 1,2-Decanediol | 0.30 | 0.30 | 0.30 | 0.30 |
| *Glycyrrhiza Inflata* Root Extract | 0.025 | 0.05 | 0.10 | 0.05 |
| Carbomer | 0.2 | 0.2 | 0.2 | 0.2 |
| Carrageenan | 0.1 | 0.1 | — | — |
| Xanthan Gum | — | — | 0.2 | 0.2 |
| Acrylates/C10-30 Alkyl Acrylate Crosspolymer | — | — | — | 0.15 |
| Sodium Polyacrylate | — | 0.2 | — | — |
| Diethylhexyl 2,6-Naphthalate | — | — | 1.0 | — |
| Phenylbenzimidazole Sulfonic acid | — | 1.0 | — | 2.0 |
| Titanium Dioxide | — | — | 1.0 | — |
| Diethylamino Hydroxybenzoyl Hexyl Benzoate | — | — | 1.0 | 1.0 |
| Octocrylene | — | 4.0 | 2.0 | 3.0 |
| 3,3,5-Trimethylcyclohexylsalicylate | — | 1.0 | — | — |
| Distarch phosphate | — | 1.0 | 1.0 | — |
| Methyl Methacrylate Crosspolymer | 1.0 | — | — | 1.0 |
| Polymethylsissesquioxane | — | — | 1.0 | 1.0 |

-continued

Formulation examples

| Chemical name | 33 % by weight | 34 % by weight | 35 % by weight | 36 % by weight |
|---|---|---|---|---|
| Acrylonitrile-methacrylonitrile-methyl-methacrylate Copolymer + Isopentane + Magnesium Hydroxide | 1.0 | 1.0 | — | — |
| 1-(1,2,3,4,5,6,7,8-Octahydro-2,3,8,8-tetramethyl-2-naphthyl)ethan-1-one | — | 0.1 | 0.1 | 0.05 |
| Hydroxyisohexyl 3-cyclohexenecarboxaldehyde | 0.05 | 0.05 | 0.1 | — |
| Linalyl Acetate | 0.1 | — | 0.05 | 0.05 |
| Perfume | 0.15 | 0.15 | 0.3 | 0.3 |
| Sodium Hydroxide | q.s. | q.s. | q.s. | q.s. |
| Water | ad 100 | ad 100 | ad 100 | ad 100 |

Formulation examples

| Chemical name | 37 % by weight | 38 % by weight | 39 % by weight | 40 % by weight |
|---|---|---|---|---|
| Polyglyceryl-10 Stearate | 0.2 | 0.2 | 0.15 | 0.15 |
| C12-15 Alkyl Benzoate | 2.5 | 2.5 | 2.0 | 3.0 |
| Isopropyl Palmitate | 2.5 | 2.5 | 2.0 | 2.0 |
| Caprylic Acid/Capric Acid Triglycerides | 2.0 | 2.5 | 1.0 | 2.0 |
| Glyceryl Stearate | 1.0 | 1.0 | 0.5 | 0.5 |
| Octyldodecanol | 0.5 | — | — | 1.0 |
| Cyclomethicone | — | — | 0.5 | 0.5 |
| Butyl Methoxydibenzoylmethane | — | 2.0 | 2.0 | — |
| Octocrylene | — | 2.0 | 3.0 | 2.0 |
| Ethylhexyl Salicylate | — | 1.0 | 1.0 | — |
| Phenylbenzimidazole Sulfonic Acid | — | 1.0 | — | 1.5 |
| Titanium Dioxide | — | 1.0 | — | 1.0 |
| 3,3,5-Trimethyl cyclohexylsalicylate | — | — | 1.0 | 1.0 |
| Glycerol | 9.0 | 5.0 | 7.0 | 7.0 |
| Tapioca Starch | 1.0 | 1.0 | — | — |
| Acrylonitrile-methacrylonitrile-methyl-methacrylate Copolymer + Isopentane + Magnesium Hydroxide | — | 1.0 | 0.5 | — |
| Aluminum Starch Octenylsuccinate | — | — | 1.0 | 1.0 |
| Distarch phosphate | — | — | — | 1.0 |
| Methylisothiazolinone | 0.05 | 0.05 | — | — |
| Phenoxyethanol | 0.5 | 0.5 | 0.4 | 0.4 |
| Benzethonium Chloride | — | — | 0.1 | — |
| Ethylhexylglycerol | — | — | 0.1 | — |
| Methylparaben | — | — | — | 0.2 |
| Carbomer | 0.25 | 0.2 | 0.2 | 0.2 |
| Acrylates/C10-30 Alkyl Acrylate Crosspolymer | 0.2 | — | — | 0.15 |
| Ammonium Acryloyldimethyltaurate/VP Copolymer | — | 0.25 | — | — |
| Sodium Polyacrylate | — | — | 0.3 | — |
| Xanthan Gum | — | — | — | 0.15 |
| 3-(Menthoxy)propane-1,2-diol | — | 0.50 | 0.10 | 0.05 |
| (1R,2S,5R)-N-(2-(2-Pyridinyl)ethyl)-2-isopropyl-5-methylcyclohexanecarboxamide | 0.10 | — | 0.05 | 0.10 |
| 1,2-Decanediol | 0.30 | 0.30 | 0.20 | 0.30 |
| Glycyrrhiza Inflata Root Extract | 0.025 | 0.05 | 0.10 | 0.05 |
| Ethanol | 3.0 | 3.0 | — | — |
| Butylene Glycol | — | — | 2.0 | 2.0 |
| Coumarin | — | 0.05 | 0.05 | — |
| Hexylcinnamal | 0.05 | 0.05 | — | 0.05 |
| Hexyl Salicylate | — | — | 0.05 | 0.05 |
| Perfume | 0.15 | 0.2 | 0.25 | 0.3 |
| Sodium Hydroxide | q.s. | q.s. | q.s. | q.s. |
| Water | ad 100 | ad 100 | ad 100 | ad 100 |

Formulation examples

| Chemical name | 41 % by weight | 42 % by weight | 43 % by weight | 44 % by weight |
|---|---|---|---|---|
| Potassium Cetylphosphate | 0.20 | 0.20 | 0.25 | 0.20 |
| C12-15 Alkyl Benzoate | 2.5 | 2.5 | 2.0 | 2.0 |
| Isopropyl Palmitate | 2.5 | 2.5 | — | 3.0 |
| Isopropyl Stearate | — | — | 2.0 | — |
| Caprylic Acid/Capric Acid Triglycerides | 2.5 | 2.5 | 1.5 | 2.0 |
| Glyceryl Stearate | 1.0 | 1.0 | 1.25 | 1.5 |
| Octyldodecanol | — | — | 1.5 | — |
| Paraffinum Liquidum | — | — | — | 1.0 |
| Glycerol | 5.0 | 7.0 | 9.0 | 6.0 |
| Bis-Ethylhexyloxyphenol Methoxyphenyl Triazines | — | 1.0 | — | 1.0 |
| Titanium Dioxide + Trimethoxycaprylylsilane | — | — | 1.0 | 1.0 |
| Phenylbenzimidazole Sulfonic Acid | — | — | 1.0 | 1.0 |
| Butyl Methoxydibenzoylmethane | 1.0 | — | 2.0 | 2.0 |
| Disodium Phenyl Dibenzimidazole Tetrasulfonate | — | 1.5 | 1.0 | — |
| Ethylhexyltriazone | 1.0 | — | — | — |
| Ethylhexyl Methoxycinnamate + BHT | 2.0 | — | — | — |
| Carbomer | — | 0.15 | 0.2 | 0.3 |
| Acrylates/C10-30 Alkyl Acrylate Crosspolymer | 0.3 | 0.1 | 0.15 | — |
| Xanthan Gum | — | — | 0.15 | 0.1 |
| Methylisothiazolinone | 0.05 | — | — | — |
| Phenoxyethanol | 0.5 | 0.5 | 0.4 | 0.4 |
| Methylparaben | — | 0.1 | — | — |
| Ethylhexyl Salicylate | — | — | 0.3 | — |
| Butylene Glycol | — | — | 3.0 | 3.0 |
| Benzethonium Chloride | — | — | — | 0.1 |
| 3-(Menthoxy)propane-1,2-diol | — | 0.50 | 0.10 | 0.05 |
| (1R,2S,5R)-N-(2-(2-Pyridinyl)ethyl)-2-isopropyl-5-methylcyclohexanecarboxamide | 0.10 | — | 0.03 | 0.10 |
| 1,2-Decanediol | 0.20 | 0.30 | 0.10 | 0.30 |
| Glycyrrhiza Inflata Root Extract | 0.025 | 0.05 | 0.10 | 0.05 |
| Linalool | 0.05 | — | — | 0.05 |
| Hexylcinnamal | 0.05 | 0.05 | — | — |
| 1-(1,2,3,4,5,6,7,8-Octahydro-2,3,8,8-tetramethyl-2-naphthyl)ethan-1-one | — | — | 0.1 | — |
| Perfume | 0.1 | 0.3. | 0.2 | 0.3 |
| BHT (tert-Butylhydroxytoluene) | 0.05 | — | — | — |
| Tocopheryl Acetate | — | 0.1 | — | — |
| Sodium Hydroxide | q.s. | q.s. | q.s. | q.s. |
| Water | ad 100 | ad 100 | ad 100 | ad 100 |

What is claimed is:

1. A topical cosmetic or dermatological preparation, wherein the preparation is suitable for the treatment and/or prophylaxis of atopic dermatitis and comprises, based on a total weight of the preparation, from 0.01 to 5.0% by weight of one or more TRPM-8 receptor agonists which comprise (1R,2S,5R)—N-(2-(2-pyridinyl)ethyl)-2-isopropyl-5-methylcyclohexanecarboxamide.

2. The preparation of claim 1, wherein the preparation further comprises one or more 1,2-alkanediols.

3. The preparation of claim 2, wherein the one or more 1,2-alkanediols comprise one or more of 1,2-heptanediol, 1,2-nonanediol, 1,2-decanediol.

4. The preparation of claim 2, wherein the one or more 1,2-alkanediols comprise 1,2-decanediol.

5. The preparation of claim 1, wherein the preparation further comprises one or more anti-erythematous and/or anti-inflammatory substances selected from licochalcone A, lignin, chroman, isoflavonoids, pentacyclic triterpenes, hamamelis, chamomile extracts, bisabolol, allantoin, calendula extracts, panthenol.

6. The preparation of claim 1, wherein the preparation further comprises licochalcone A.

7. The preparation of claim 6, wherein the preparation comprises a *Glycyrrhiza Inflata* Root extract that contains licochalcone A.

8. The preparation of claim 1, wherein the preparation comprises, based on a total weight of the preparation, from 0.02 to 5.0% by weight of one or more polyols selected from 1,2-pentanediol, 1,2-hexanediol, 1,2-heptanediol, 1,2-octanediol, 1,2-nonanediol, 1,2-decanediol, and from 0.01 to 5.0% by weight of one or more anti-erythematous or anti-inflammatory substances selected from licochalcone A, lignin, chroman, isoflavonoids, pentacyclic triterpenes, hamamelis, chamomile extracts, bisabolol, allantoin, calendula extracts, panthenol.

9. The preparation of claim 1, wherein the preparation comprises, based on a total weight of the preparation, from 0.02 to 5.0% by weight of one or more polyols which comprise 1,2-decanediol, and from 0.01 to 5.0% by weight of one or more anti-erythematous or anti-inflammatory substances which comprise licochalcone A.

10. A method for the treatment or alleviation of atopic dermatitis in a patient in need thereof, wherein the method comprises applying the preparation of claim 1 onto skin affected by atopic dermatitis in an amount which is effective for treating or alleviating atopic dermatitis.

11. The method of claim 10, wherein the preparation further comprises menthoxypropanediol.

12. A topical cosmetic or dermatological preparation, wherein the preparation is suitable for the treatment and/or prophylaxis of atopic dermatitis and comprises, based on a total weight of the preparation, from 0.01 to 5.0% by weight of one or more TRPM-8 receptor agonists which comprise one or more of linalool, geraniol, hydroxycitronellal, 1,4-dioxaspiro[4.5]-decane-2-methanol, 5-methyl-2-prop-1-en-2-ylcyclohexan-1-ol, (1R,2S,5R)—N-(2-(2-pyridinyl)ethyl)-2-isopropyl-5-methylcyclohexanecarboxamide, from 0.02 to 5.0% by weight of one or more polyols selected from 1,2-pentanediol, 1,2-hexanediol, 1,2-heptanediol, 1,2-octanediol, 1,2-nonanediol, 1,2-decanediol, and from 0.01 to 5.0% by weight of one or more anti-erythematous or anti-inflammatory substances selected from licochalcone A, lignin, chroman, isoflavonoids, pentacyclic triterpenes, hamamelis, chamomile extracts, bisabolol, allantoin, calendula extracts, panthenol.

13. The preparation of claim 12, wherein the one or more TRPM-8 receptor agonists comprise one or more of 1,4-dioxaspiro[4.5]-decane-2-methanol, 5-methyl-2-prop-1-en-2-ylcyclohexan-1-ol, (1R,2S,5R)—N-(2-(2-pyridinyl)ethyl)-2-isopropyl-5-methylcyclohexanecarboxamide.

14. The preparation of claim 12, wherein the one or more TRPM-8 receptor agonists additionally comprise menthoxypropanediol.

15. The preparation of claim 12, wherein the one or more polyols comprise 1,2-decanediol.

16. The preparation of claim 12, wherein the one or more anti-erythematous or anti-inflammatory substances comprise licochalcone A.

17. The preparation of claim 16, wherein the preparation comprises a *Glycyrrhiza Inflata* Root extract that contains licochalcone A.

18. The preparation of claim 12, wherein the preparation comprises, based on a total weight of the preparation, from 0.02 to 5.0% by weight of one or more polyols which comprise 1,2-decanediol, and from 0.01 to 5.0% by weight of one or more anti-erythematous or anti-inflammatory substances which comprise licochalcone A.

19. A method for the treatment or alleviation of atopic dermatitis in a patient in need thereof, wherein the method comprises applying the preparation of claim 12 onto skin affected by atopic dermatitis in an amount which is effective for treating or alleviating atopic dermatitis.

20. The method of claim 19, wherein the preparation further comprises menthoxypropanediol.

\* \* \* \* \*